US010478582B1

(12) United States Patent
Schroeder et al.

(10) Patent No.: US 10,478,582 B1
(45) Date of Patent: *Nov. 19, 2019

(54) ADAPTOR FOR BREATHING TUBE AND METHOD

(71) Applicant: Barthel LLC, Wauwatosa, WI (US)

(72) Inventors: Mark E. Schroeder, Madison, WI (US); Timothy Patrick Barry, Middleton, WI (US); Evan James Joyce, Brookfield, WI (US); Ryan Ross Childs, Ham Lake, MN (US); Ozair Iqbal Chaudhry, Dubai (AE)

(73) Assignee: Barthel LLC, Wauwatosa, WI (US)

( * ) Notice: Subject to any disclaimer, the term of this patent is extended or adjusted under 35 U.S.C. 154(b) by 1064 days.

This patent is subject to a terminal disclaimer.

(21) Appl. No.: 14/793,724

(22) Filed: Jul. 7, 2015

Related U.S. Application Data

(63) Continuation of application No. 13/037,818, filed on Mar. 1, 2011, now Pat. No. 9,084,864, which is a continuation-in-part of application No. 12/717,431, filed on Mar. 4, 2010, now abandoned.

(51) Int. Cl.
*A61M 16/08* (2006.01)
*A61M 15/00* (2006.01)

(52) U.S. Cl.
CPC ...... *A61M 16/0816* (2013.01); *A61M 15/009* (2013.01); *A61M 15/0068* (2014.02)

(58) Field of Classification Search
CPC .......... A61M 16/0816; A61M 15/0068; A61M 15/009; A61M 15/0071
See application file for complete search history.

(56) References Cited

U.S. PATENT DOCUMENTS

| 5,482,030 | A | * | 1/1996 | Klein | ................ | A61M 15/009 116/308 |
| 2007/0284383 | A1 | * | 12/2007 | Wright | .................. | G06M 1/00 221/7 |
| 2010/0101570 | A1 | * | 4/2010 | Meyer | ............... | A61M 15/0065 128/203.12 |

* cited by examiner

*Primary Examiner* — Tan-Uyen T Ho
*Assistant Examiner* — Jonathan S Paciorek
(74) *Attorney, Agent, or Firm* — Barthel LLC; Renée C. Barthel

(57) ABSTRACT

The present disclosure provides a universal breathing tube adaptor that can accept or otherwise accommodate a metered dose canister (MDC) having a variety of shapes, structures, sizes, and/or configurations. The present breathing tube adaptor includes a sidewall which defines a chamber. A conduit extends from the chamber through a floor of the device for discharging aerosolized medicament from the MDC. The sidewall includes opposing exposed edges which define a channel. The sidewall supports the MDC when it is invertingly inserted into the chamber. The channel permits structure of an MDC to extend radially outward through the channel and outside the chamber thereby enabling the valve stem of the MDC to engage the conduit.

19 Claims, 9 Drawing Sheets

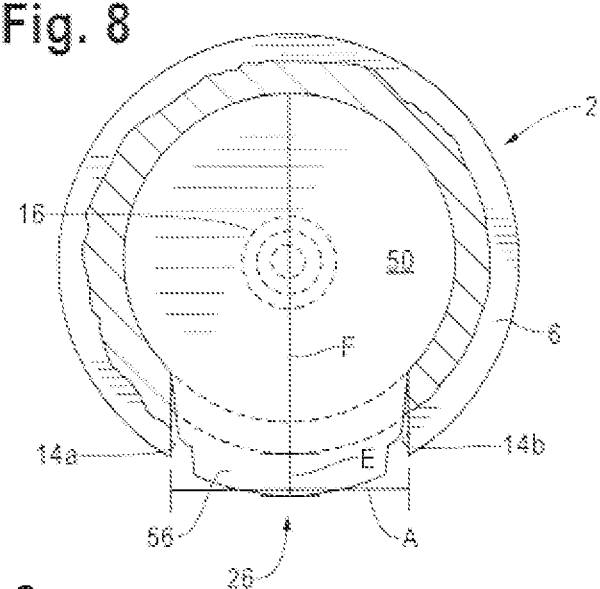
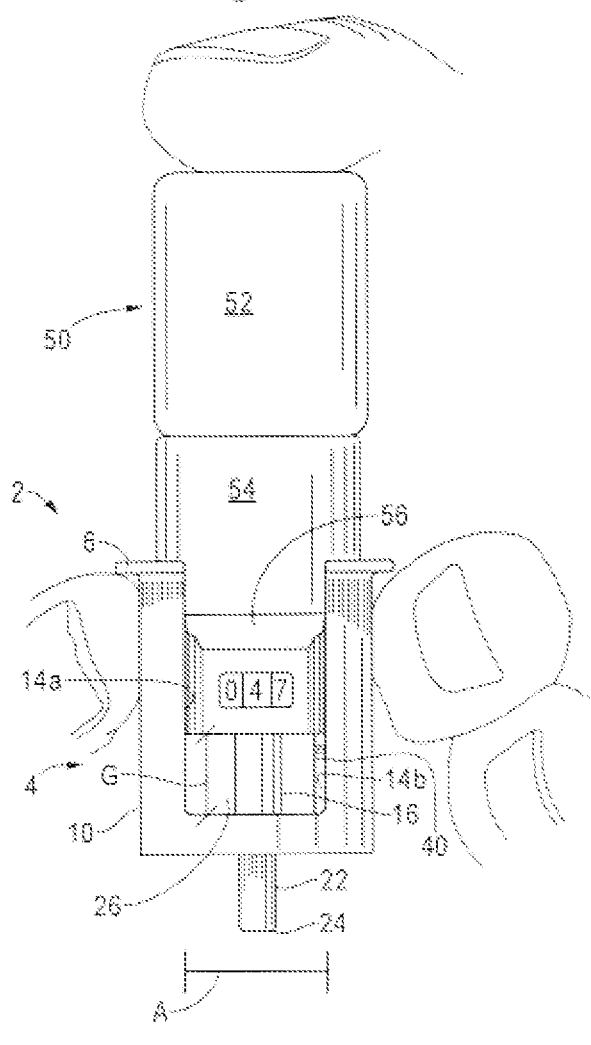
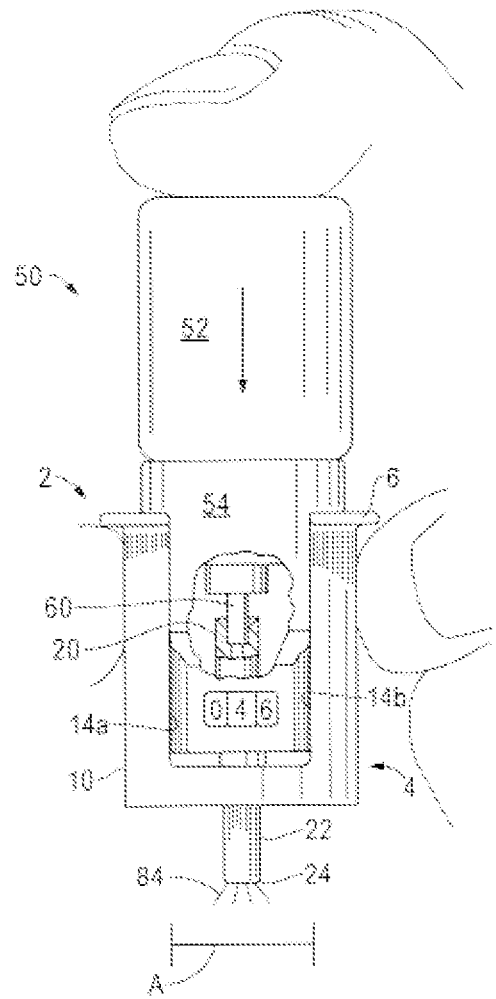

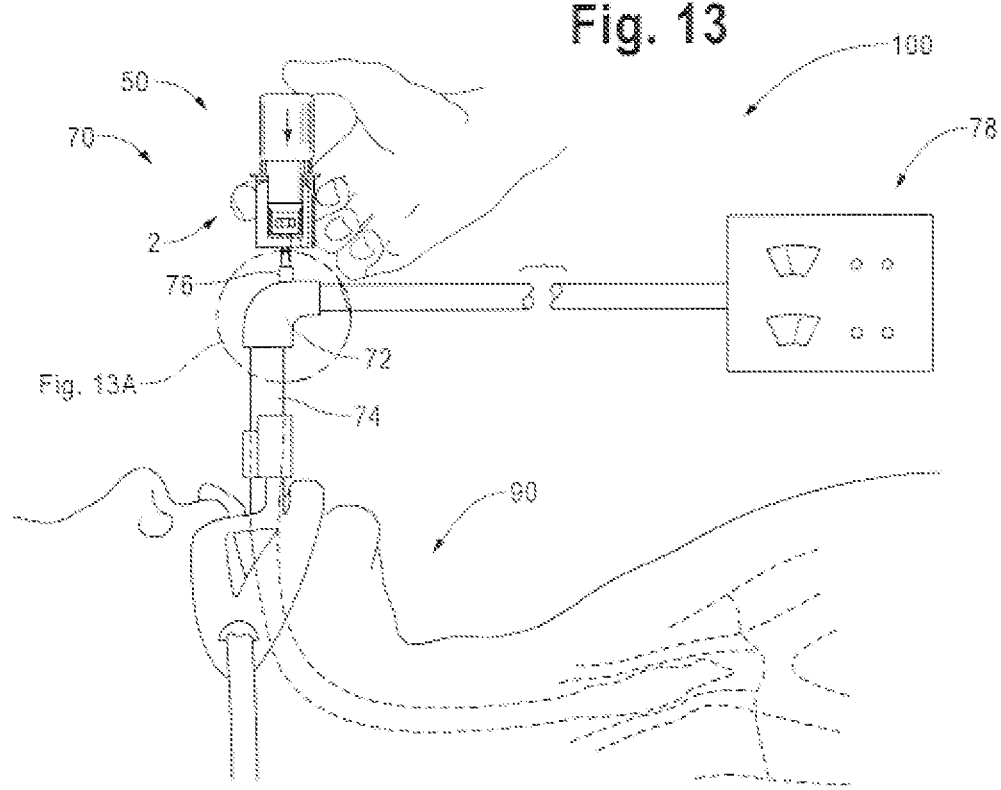
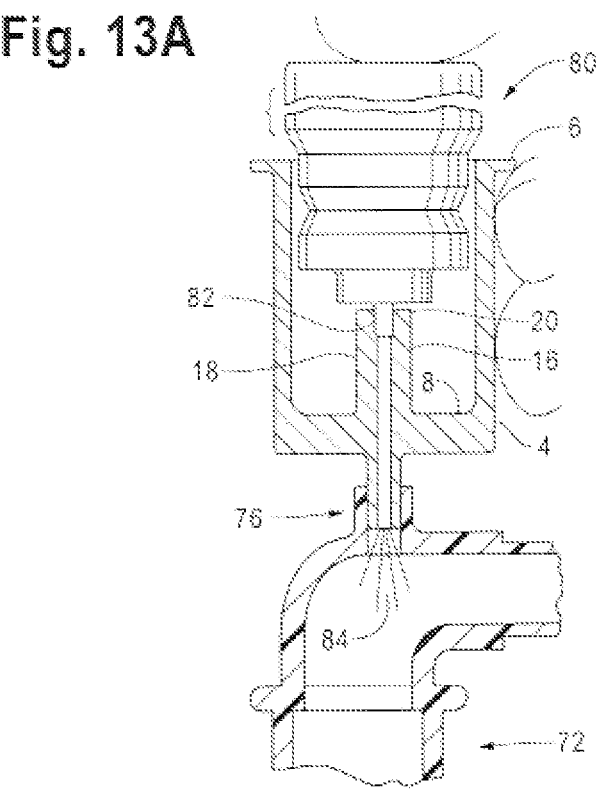

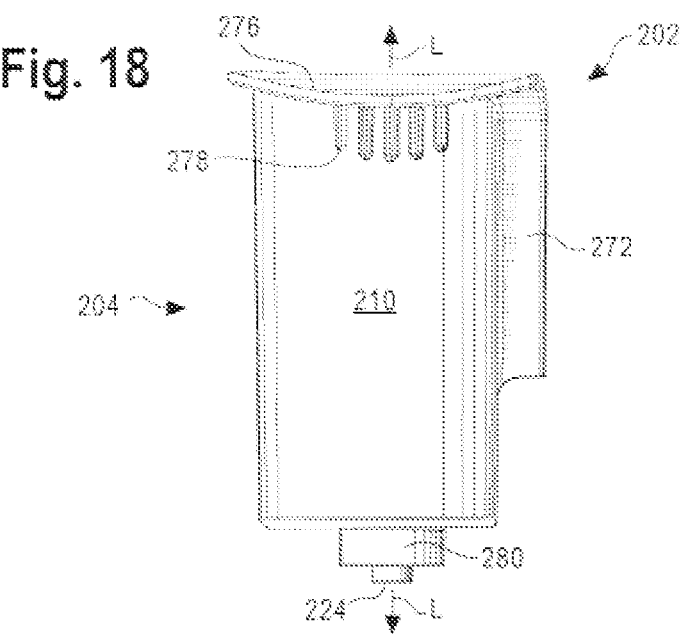
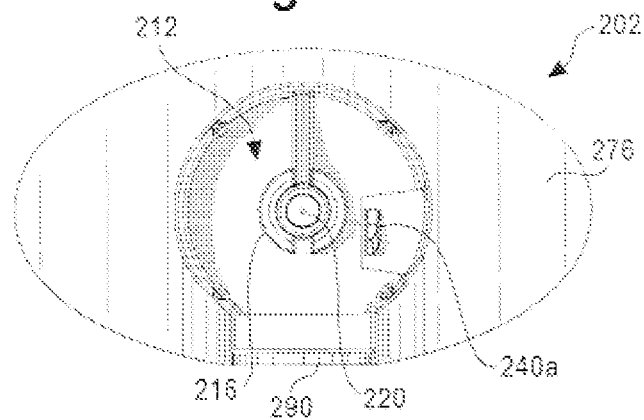
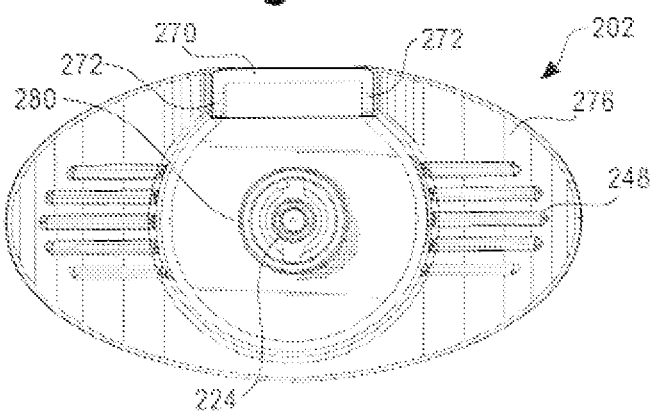

US 10,478,582 B1

ADAPTOR FOR BREATHING TUBE AND METHOD

PRIORITY

This application is a continuation application of U.S. patent application Ser. No. 13/037,818 filed on Mar. 1, 2011, which is a continuation-in-part application of U.S. patent application Ser. No. 12/717,431 filed on Mar. 4, 2010, the entire contents of both applications which are incorporated by reference herein.

BACKGROUND

The present disclosure relates to a device for administering aerosolized medicament to a person.

Administration of aerosolized medicament from a metered-dose canister (MDC) for treating an intubated person experiencing respiratory distress is known. Typically, the MDC is directly or indirectly connected to a breathing tube. The MDC is subsequently actuated to discharge a "puff" of the drug into the breathing tube for action on the breathing passages and absorption through the person's lungs. An adaptor is often used to connect the MDC with the breathing tube to ensure proper dispensing of the drug.

Recent structural changes to MDCs, however, have created obstacles to effective administration of aerosolized medicament to an intubated patient. Many MDCs now include a housing attached to the top portion thereof. The housing oftentimes wholly or partially surrounds the valve stem. The housing prevents proper connection between the MDC and the adaptor which, in turn, prevents discharge of the medicament from the MDC into the breathing tube. In addition, the size and shape of many MDCs has changed as the propellant is changed from chlorinated fluorocarbons in favor of hydro-fluoroalkanes. Thus, compatibility no longer exists between conventional breathing tube adaptors and myriad MDCs having different sizes, shapes, and/or configurations.

A need exists for an adaptor that can accommodate MDCs with different shapes, structures, sizes, and/or configurations for delivery of medicament therefrom to an intubated person. A need further exists for a breathing tube adaptor that can dispense aerosolized medicament into a breathing tube from an MDC having (1) a top-portion housing structure and/or (2) an MDC with no top-portion housing structure, and/or (3) an MDC with structure that extends radially outward beyond the diameter of the canister.

SUMMARY

The present disclosure provides an adaptor that can accept or otherwise accommodate an MDC having a variety of shapes, structures, sizes, and/or configurations. The present adaptor delivers aerosolized medicament from many different types of MDCs into a breathing tube to treat an intubated person. The present adaptor is easy-to-use which directly contributes to quick, reliable, and effective aerosolized medicament administration—which is especially advantageous in emergency situations.

The present disclosure provides a device. In an embodiment, a device (or adaptor) for delivering a medicament into a breathing tube from a counter metered-dose canister (CoMDC) is provided. The CoMDC includes a valve stem and a counter window. The device includes a substantially cylindrical body with a top rim, a floor, and an arcuate sidewall. The arcuate sidewall extends between the top rim and the floor. The body defines a chamber. The chamber is adapted to receive an inverted CoMDC. The device also includes a conduit extending from the chamber through the floor. The conduit includes a well located within the chamber. The well is adapted to engage the valve stem. The conduit also includes a discharge port disposed below the floor for dispensing aerosolized medicament from the CoMDC. The arcuate sidewall includes opposing exposed edges which define a channel. The channel extends from the top rim substantially to the floor. The channel is adapted to permit longitudinal movement of the counter window as the valve stem moves into engagement with the conduit well.

In an embodiment, the device includes an inverted CoMDC located inside the chamber.

The present disclosure provides an assembly. In an embodiment, an assembly for delivering medicament from a metered-dose canister (MDC) is provided. The MDC includes a valve stem. The assembly includes the device as disclosed above. The assembly also includes a breathing tube connector. The breathing tube connector has an inlet. The inlet is in fluid communication with the discharge port of the device. The inlet receives medicament dispensed from the MDC.

In an embodiment, the assembly includes an inverted MDC or inverted CoMDC located inside the chamber of the device.

The present disclosure provides a method. In an embodiment, a method for administering medicament from a metered-dose canister (MDC) to an intubated patient is provided. The method includes invertingly inserting the MDC into a device. The device has the structure as disclosed above. The method includes placing the discharge port in fluid communication with an inlet of a breathing tube and reciprocally engaging the MDC valve stem with the conduit well of the device. The method further includes dispensing aerosolized medicament from the MDC through the conduit into the breathing tube and into the lungs of the intubated patient. In an embodiment, the breathing circuit includes the assembly disclosed above.

The present disclosure provides a system. In an embodiment, a system is provided and includes a breathing circuit. The present device and/or assembly is a component of the breathing circuit.

An advantage of the present disclosure is an improved breathing tube adaptor.

An advantage of the present disclosure is an improved method for administering an aerosolized medicament to an intubated patient.

An advantage of the present disclosure is an adaptor with versatility for administering aerosolized medicament from a MDC, a C-MDC, and/or a CoMDC.

An advantage of the present disclosure is the provision of a breathing tube adaptor that is ergonomically friendly.

An advantage of the present disclosure is an adaptor that is easy to use and quickly delivers aerosolized medicament from an MDC into a breathing tube.

An advantage of the present disclosure is a universal adaptor that can disperse aerosolized medicament to an intubated patient for many different types of metered dose canisters having a variety of shapes, sizes and/or configurations.

DESCRIPTION OF THE FIGURES

FIG. 8 is a top plan view of the CoMDC in a device in accordance with an embodiment of the present disclosure.

FIG. 9 is a front elevation view of a CoMDC in a device in accordance with an embodiment of the present disclosure.

FIG. 10 is a front elevation view (and partial sectional view) of the CoMDC in the device of FIG. 9, the device dispensing a medicament in accordance with an embodiment of the present disclosure.

FIG. 13 is a representation showing a system and a method for administering medicament to an intubated person in accordance with an embodiment of the present disclosure.

FIG. 13A is an enlarged sectional view of area 13A of FIG. 13 in accordance with an embodiment of the present disclosure.

FIG. 18 is a right side elevation of the device of FIG. 14 in accordance with an embodiment of the present disclosure.

FIG. 19 is a top plan view of the device of FIG. 14 in accordance with an embodiment of the present disclosure.

FIG. 20 is a bottom plan view of the device of FIG. 14 in accordance with an embodiment of the present disclosure.

DETAILED DESCRIPTION

Figure 1:
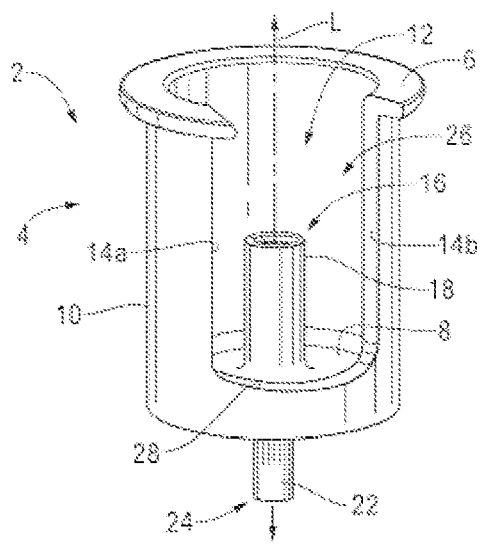
FIG. 1 is a perspective view of a device (adaptor) in accordance with an embodiment of the present disclosure.

The present disclosure provides a device. The device delivers a medicament from a metered-dose canister to a breathing tube. In this sense, the device is an "adaptor," that is, an object which enables a metered-dose canister to operate with, or fluidly communicate with, or otherwise fit together with a breathing circuit. Accordingly, the term "device," "adaptor," "breathing tube adaptor" are used interchangeably.

A "metered-dose canister" or "MDC" is a dispensing device that delivers a specific (i.e., metered) dose of medicament to the airways and lungs of a mammal (typically a human) in the form of an aerosol spray or cloud containing fine particles of the medicament (liquid or solid). The MDC includes a container (typically cylindrical in shape) in which a medicament (particulate solid and/or liquid) and a pressurized propellant reside. Other nonlimiting components that may be in the container include surfactant, preservative, and/or flavorant. A valve stem extends from a top portion of the container. The valve stem, typically spring loaded, is normally biased to be in a closed position, or an extended position, unless when actuated by a user or medical professional. Actuation typically is induced by depressing the valve stem against or into a dispensing device. Each depression typically administers only one metered (or measured) dose of medicament. The metered discharge of the aerosolized medicament is often referred to as a short "burst" or "puff." The spring bias returns the valve stem to a closed position, readying the MDC for application of another metered dose, as needed. The MDC is typically inverted (i.e., valve stem down) for administration through a dispensing device. Throughout this description, the terms "metered-dose" and "multi-dose" are used interchangeably and denoted by the acronym "MD."

A "capped metered dose canister" (or "C-MDC") is an MDC with a housing attached to the top. The housing surrounds (fully or partially) the valve stem. The housing includes an orifice through which the valve stem extends. One nonlimiting type of C-MDC is a "counter MD" canister (or "CoMDC"). A "CoMDC" includes a counter device in the housing, a counter port for receiving a counter actuator, and a counter window which displays the number of doses remaining in the CoMDC. With each actuation of the CoMDC, a counter actuator present in a dispensing device operatively engages the counter device and increments a counter displayed through the counter window. The counter indicates the number of doses remaining (or the number of doses administered) through the counter window.

The "medicament" is a solid (fine particulate), a liquid, a gas, and combinations thereof. Nonlimiting examples of suitable medicaments for use with the MDC include bronchodilators, drugs for treating chronic obstructive pulmonary disease, albuterol, as well as other types of medications (including other compositions and any blends of the foregoing) that are suitable for delivery via a MDC or a CoMDC. Such delivery is aided by the propellant. The propellant delivers the medicament as an aerosol spray or cloud. Nonlimiting examples of suitable propellants include chlorofluorocarbons (CFC) and hydrofluoroalkanes (HFA). HFA is advantageous as it does not degrade ozone. Nonlimiting examples of suitable medicaments include fluticasone (Flovent), triamcinolone (Azmacort), flunisolide (Aerobid), beclomethasone (Qvar), cromolyn (Intal), nedocromil (Tilade), albuterol (AccuNeb, Proventil, Ventolin), levalbuterol (Xopenex), pirbuterol (Maxair), ipratropium (Atrovent), salmeterol (Serevent), and any combination thereof.

The present device delivers medicament from the MDC into a breathing tube. A "breathing tube," as used herein, is a tube placed in a body orifice to provide a passageway to the lungs of a mammal (such as a person). Nonlimiting types of breathing tubes include an endotracheal tube, a nasotracheal tube, and a tracheal tube (and intubation tubes, stoma insertion tubes). An "endotracheal tube" is a breathing tube that passes through the mouth, the larynx, the vocal cords, into the trachea. A "nasotracheal tube" is a breathing tube that passes through the nose, the larynx, the vocal cords, and the trachea. A "tracheal tube" is a breathing tube inserted into the trachea. A breathing tube is used to ventilate, aspirate, respirate, oxygenate, and/or anesthetize a patient. A breathing tube is not an inhaler, such as a typical boot-type asthma inhaler. An "inhaler" (such as an asthma inhaler), as used herein, is a portable device and is not affixed to a person. An inhaler has a port for receiving an MDC and a boot-shaped structure with an expansive exhaust port to maximize the volume of discharge aerosolized medicament that is delivered to a user's mouth. The expansive exhaust port maximizes the volume of the aerosolized spray and is not adapted for connection with a breathing tube. The present device is not an inhaler.

The term "intubation" (or "intubate") is the placement of a breathing tube in a body orifice. Accordingly, an "intubated patient" is a person with a breathing tube affixed to or otherwise inserted through a body orifice that fluidly communicates with the trachea. An intubated patient may be conscious, unconscious, and/or anesthetized. Intubation may occur before, during, and/or after surgery. A nonlimiting situation where intubation occurs is in an intensive care unit to provide and/or support ventilation for a patient.

In an embodiment, a device (or adaptor) 2 for delivering a medicament from a CoMDC into a breathing tube is provided as shown in FIGS. 1-5. The device 2 includes a body 4, a top rim 6, a floor 8, and a sidewall 10. The sidewall 10 is arcuate and extends between the top rim 6 and the floor 8 and provides the body 4 with a substantially cylindrical, or cylindrical, shape. The body 4 defines a substantially cylindrical, or cylindrical, chamber 12. The chamber 12 is adapted to receive an inverted MDC (or inverted C-MDC), or an inverted CoMDC, as will be discussed below. The sidewall includes opposing exposed edges 14a, 14b. The device 2 also includes a conduit 16.

Figure 2:
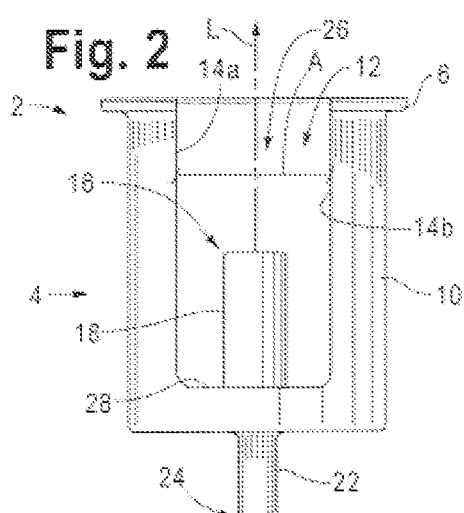
FIG. 2 is front elevation view of the device of FIG. 1.
Figure 3:
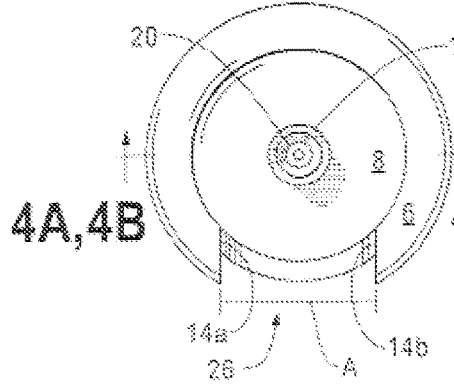
FIG. 3 is a top plan view of the device of FIG. 1.

As shown in FIGS. 1-3, the conduit 16 is annular and extends from the chamber 12, through the floor 8, and below the floor 8. The conduit 16 vertically extends from the chamber 12, through the floor 8 and vertically below the floor 8. The conduit 16 is centrally located in chamber 12 as shown in FIG. 3. The conduit 16 has an upper portion 18 disposed or otherwise located in the chamber 12. A well 20 is located at the top of the upper portion 18. The well 20 is located within the chamber 12 and is adapted to receive or otherwise engage the valve stem of an inverted MDC/C-MDC/CoMDC, as will be described below. A lower portion 22 of the conduit 16 includes a discharge port 24 and is vertically disposed or otherwise located below the floor 8. The discharge port 24 is configured to dispense aerosolized medicament. The conduit 16, the well 20, and discharge port 24 are configured to convey aerosolized medicament expelled from a valve stem of the MDC and to an intubated patient by way of a breathing tube.

The top rim 6 extends radially outward from a longitudinal axis L that extends through the conduit 16 as shown in FIGS. 1 and 2. The top rim 6 has a width from about 3 mm to about 10 mm, or from about 4 mm to about 6 mm. The top rim 6 advantageously provides a comfortable finger support for the device 2. The top rim 6 also advantageously provides an ergonomically favorable finger and hand posture for comfortably actuating a MDC/C-MDC/CoMDC.

The sidewall 10 includes exposed edge 14a and exposed edge 14b in opposing relation to each other. Opposing exposed edges 14a, 14b extend from the top rim 6, or from the top of the body 4, and extend longitudinally downward to, or substantially to, the floor 8. Exposed edge 14a opposes exposed edge 14b as shown in FIGS. 1, 2, 3 and 5. Exposed edge 14a is parallel to, or substantially parallel to, exposed edge 14b.

The opposing exposed edges 14a, 14b define a channel 26 in the sidewall 10 as shown in FIGS. 1, 2, 3 and 5. A "channel," as used herein, is a passage in the sidewall 10 extending from the top rim 6 to, or substantially to, the floor 8. The channel 26 permits longitudinal passage or longitudinal travel of a counter window as an inverted CoMDC is loaded into the chamber 12 as will be described below. The counter window longitudinally moves along the channel as the valve stem of the inverted CoMDC moves into engagement with the conduit well. Longitudinal movement is movement along and/or parallel to, or substantially parallel to, longitudinal axis L.

The dimensions of the opposed exposed edges 14a, 14b and the resultant channel 26 may be varied. In an embodiment, the opposing exposed edges 14a, 14b extend substantially to the floor 8 to form a lip portion 28 of the sidewall. Alternatively, the opposing exposed edges may extend from the top rim 6 all the way to the floor 8, thereby omitting the lip portion from the sidewall. A distance A (FIGS. 2, 3, 8-10) between the opposing edges 14a, 14b may be varied which concomitantly varies the width of the channel 26.

The opposing exposed edges 14a, 14b form a profile or an outline shape. The profile formed by the opposing exposed edges 14a, 14b and/or the channel 26 may vary. Nonlimiting examples of profiles or outlines that can be formed by opposing exposed edges 14a, 14b and/or the channel 26 include, a "U-shape" profile a "blocked U-shape" profile, a square outline, a rectangular outline, an arc shape profile/outline, and an elliptical shape profile/outline. In an embodiment, the opposing exposed edges 14a, 14b form a U-shaped profile as shown in FIGS. 1-2.

Nonlimiting dimensions for the following components are provided in Table 1 below.

TABLE 1

| Component | Dimension |
| --- | --- |
| Body 4 | Longitudinal length 30 mm-40 mm |
| Top rim 6 | Radial width 3 mm-6 mm |
| Floor 8 | Thickness 2 mm-6 mm |
| Sidewall 10 | Longitudinal length |
|  | Inner 30 mm-34 mm |
|  | Outer 30 mm-40 mm |
| Chamber 12 | Diameter 20 mm-30 mm |
| Exposed edge 14a, 14b | Longitudinal length 28 mm-36 mm |
| Conduit 16 | Longitudinal length 20 mm-40 mm |
|  | Outer diameter 4 mm-mm |
|  | Inner diameter 0.5 mm-3 mm |
| Upper portion of conduit 18 | 10 mm-20 mm |
| Well 20 | Diameter 1 mm-3 mm |

TABLE 1-continued

| Component | Dimension |
| --- | --- |
| Channel 26 | Width (or length of A) 10 mm-18 mm |

Figure 4A:
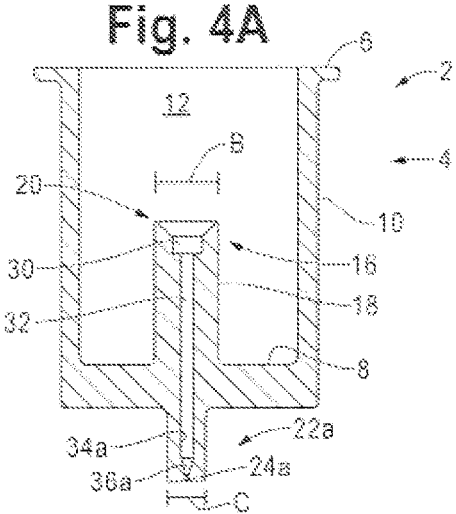
FIG. 4A is a sectional view taken along line 4A-4A of the device of FIG. 3 in accordance with an embodiment of the present disclosure.

FIG. 4A is a sectional view of an embodiment of the device 2 taken along line 4A-4A of FIG. 3. The outer diameter for conduit upper portion 18 and conduit lower portion 22 may be the same or different. In an embodiment, the outer diameter B of conduit upper portion 18 is greater than the outer diameter C for the conduit lower portion 22.

The well 20 is annular and defines a frustoconical block to engagingly receive the valve stem of an inverted MDC/C-MDC/CoMDC. The well 20 gradually tapers or narrows to an intermediate cylindrical section 30 and then narrows further to an upper passageway 32 defined along the upper portion 18. The well 20, intermediate section 30 and the upper passageway 32 define cross-sectional diameters of D1, D2 and D3, having successively smaller diameters. The upper passageway 32 in FIGS. 4A and 4B fluidly communicates with a lower passageway located in the conduit lower portion 22.

The cross-sectional diameter of the passageway extending through the conduit 16 may be modified to facilitate a desired spray pattern, and/or a desired spray velocity, and/or a desired spray volume. The diameter of the upper passageway 32 and/or lower passageway may vary or may be constant. Similarly, the diameter of the upper passageway 32 may be the same as, or different than, the diameter of the lower passageway.

In an embodiment, the diameter of upper passageway 32 is the same as, or substantially the same as, the diameter of the lower passageway 34a as shown in FIG. 4A. The lower passageway 34a ends at the discharge port 24a. The distal end of the passageway 34a narrows to a distal spray section 36a that ejects a fine directional spray of the aerosolized medicament through the discharge port 24a. The discharge port 24a discharges a directional burst of the aerosolized medicament into a breathing tube. The conduit lower portion 22a may have a length from about 5 mm to about 100 mm, or from about 7 mm to about 50 mm, or about 9 mm. In an embodiment, the conduit lower portion 22a tapers as it extends distally from the bottom of the floor 8. This provides a conduit lower portion 22a with a taper to create a friction fit with a Luer port, as will be discussed below.

Figure 4B:
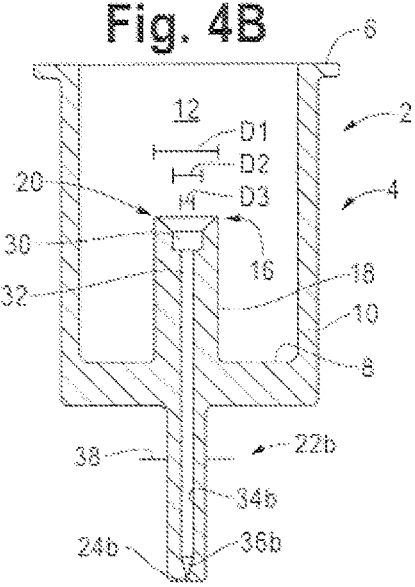
FIG. 4B is a sectional view taken along line 4B-4B of the device of FIG. 3 in accordance with an embodiment of the present disclosure.

FIG. 4B is a sectional view taken along line 4B-4B of FIG. 3 and shows another embodiment for the conduit lower portion. The conduit upper portion 18 in FIGS. 4A and 4B may have the same or different dimensions. In FIG. 4B, a conduit lower portion 22b includes a lower passageway 34b which gradually tapers or narrows to a distal spray section 36b that ejects a fine directional spray of the aerosolized medicament through the discharge port 24b. The directional spray profile provided by conduit lower portion 22a and/or 22b is distinct from the dissipated or disperse spray profile emitted from an inhaler, such as an asthma inhaler. The directional spray pattern provided by conduit lower portion 22a and/or 22b is distinct from the spray profile emitted from a bare valve stem of an MDC.

Either conduit lower portion 22a or 22b may include a collar 38 that circumferentially surrounds the conduit lower portion. The collar 38 extends radially outwardly from the exterior surface of the conduit lower portion. The collar 38 forms a tight seal when the device 2 is inserted into an inlet of a breathing tube as will be discussed below.

In an embodiment, the conduit lower portion 22b has a length from about 5 mm to about 100 mm, or from about 9 mm to about 50 mm, or about 25 mm.

The configuration of the conduit 16 and conduit lower portion 22a, 22b in particular increase the spray duration for the expelled aerosol compared to (i) the aerosol cloud expelled from a bare MDC and/or (ii) an aerosol cloud expelled from an MDC in a conventional adaptor. Bounded by no particular theory, it is believed that the length of the conduit 16 and/or the diameter of the inner passageway of the conduit 16 constrains the spray emitted from the valve stem. This produces an extended spray duration. In an embodiment, an MDC actuated with the present device produces a spray duration greater than about 1 second to about 6 seconds, or greater than 2 seconds to about 5 seconds, or greater than 3 seconds to about 5 seconds.

The extended spray duration provided by the present device is advantageous. A person's inhaled breath (or a pressurized ventilator breath) occurs over several seconds. An extended spray duration, timed to begin at the start of inspiration, more effectively carries aerosolized medicament out the end of the endotracheal tube to the airways and to the lungs where it has its effect. The extended spray duration produced by the present device advantageously spreads the aerosol spray over more of the breath, providing a desired "spacing" effect.

The conduit lower portion 22a, 22b also directs the aerosol spray into the interior of the breathing tube connector, avoiding collection of the spray on the breathing tube interior surfaces. The directional spray produced by the present device gets more medicament to the patient's lungs compared to the disperse cloud expelled by a bare valve stem of an MDC inserted into a breathing circuit, for example.

Figure 5:
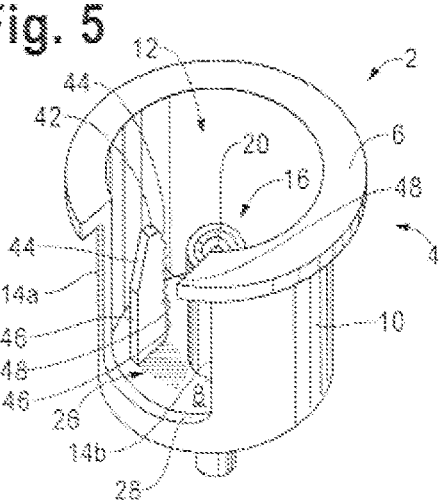
FIG. 5 is perspective view of a device in accordance with an embodiment of the present disclosure.
Figure 7:
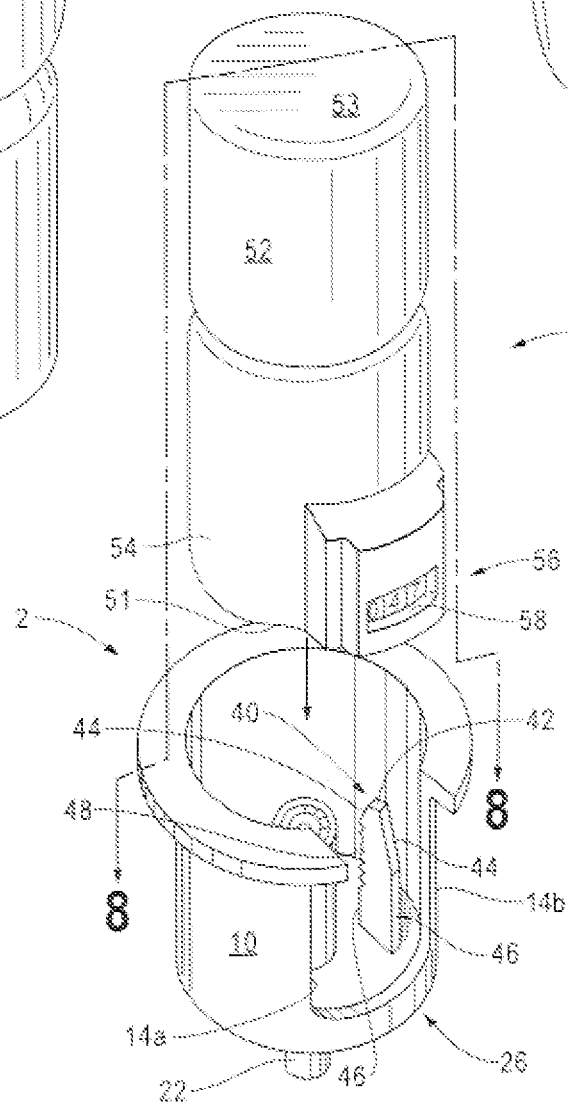
FIG. 7 is a perspective view of an inverted CoMDC of FIGS. 6A and 6B, the inverted CoMDC being inserted into a device in accordance with an embodiment of the present disclosure.

In an embodiment, the device 2 includes a counter actuator 40 as shown in FIGS. 5, 7 and 9. The counter actuator may be located anywhere on the floor 8 so as to be positioned to operatively engage with a counter port and a counter device on an inverted CoMDC. For example, the counter actuator is located at a first position in FIG. 5 and the counter actuator is located at a second position in FIG. 7. The counter actuator 40 extends upwardly from the floor 8 and is adapted to engage and actuate a counter of the CoMDC. As shown in FIGS. 5 and 7, counter actuator 40 includes a horizontal top edge 42, tapered upper side edges 44, and opposing lower side edges 46. One or both of the side edges 46 may include actuator teeth 48, as shown in FIGS. 5 and 7.

Figure 6A:
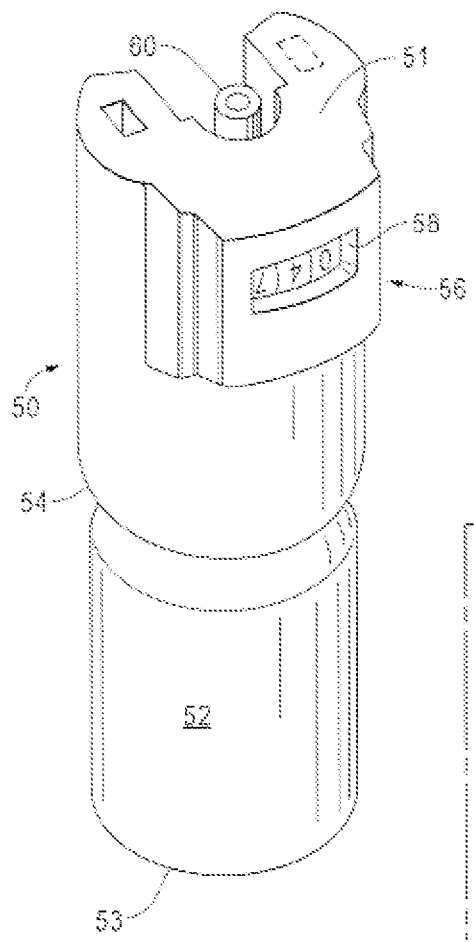
FIG. 6A is perspective view of a counter metered dose canister (CoMDC).
Figure 6B:
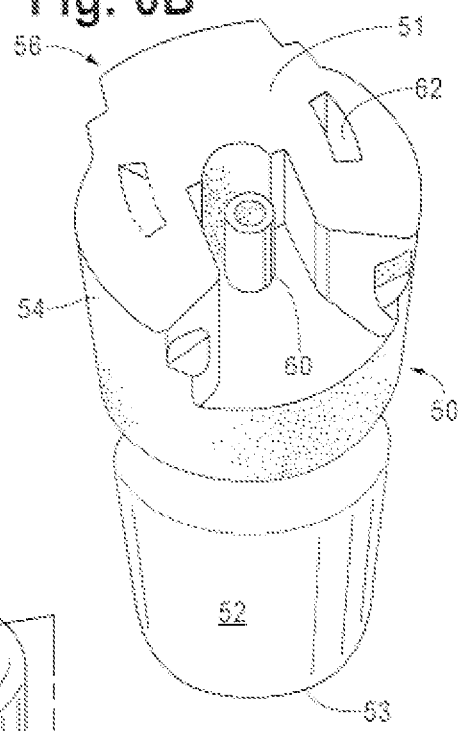
FIG. 6B is a top perspective view of the CoMDC of FIG. 6A.

The device 2 is configured or otherwise adapted to receive an MDC, a C-MDC, or a CoMDC. In other words, the device 2 is configured to operatively communicate with either an MDC, a C-MDC, or a CoMDC and dispense an aerosolized medicament. In an embodiment, the device 2 is adapted to receive a CoMDC. Turning to FIGS. 6-10, the device 2 is shown together with a CoMDC 50. The CoMDC 50 includes a cylindrical, or substantially cylindrical, container 52 having a top 51 and a bottom 53. A housing 54 is attached to the top of the container 52. The housing 54 includes a counter device therein (not shown), a counter window 56 through which a counter 58 is displayed. The counter 58 indicates the number of metered dosages remaining (or the number of metered doses administered). A valve stem 60 extends from the top of the container 52 and through the housing 54. A counter opening 62 receives a counter actuator for incrementing the counter, as shown in FIG. 6B, the counter opening 62 may be on either side (second location shown in phantom) of the housing 54.

As shown in FIG. 8, the counter window 56 provides the CoMDC 50 with a maximum diameter E that is greater than the diameter F of the chamber 12. The term "maximum diameter," as used herein, is the longest length between two opposing points along the outermost perimeter of the CoMDC 50 taken from a plane view. In an embodiment, the maximum diameter for CoMDC 50 is diameter E from the counter window 56 to the opposing side, taken from a plan view.

As shown in FIG. 8, the counter window 56 extends radially outwardly beyond the diameter of the chamber 12, and may extend beyond the outer diameter of the body 4. FIG. 8 shows that the maximum diameter E for the CoMDC is greater than the diameter F for the chamber 12. The distance A between the opposing exposed edges 14a, 14b is configured so that the channel 26 has a width suitable to allow free passage of the counter window 56 longitudinally along the channel 26. Although only the counter window is shown extending through the channel, it is understood that other structures or radial protrusions of an MDC, a C-MDC, or a CoMDC may also extend between the opposing exposed edges 14a, 14b and radially outward through the channel 26.

In this way, the device 2 is adapted to receive the CoMDC 50 even though the CoMDC 50 has a maximum diameter greater than the diameter of the chamber 12. The inverted CoMDC 50 travels unobstructed through the chamber 12 until the valve stem 60 engages the conduit well 20 as shown in FIG. 10. The counter actuator 40 also engages the counter device, as shown in FIGS. 9-10. The bottom of the inverted CoMDC 50 may then be depressed, reciprocally engaging the valve stem 60 with the well 20 to dispense a metered dose of aerosolized medicament 84 through the conduit 16, out of discharge port 24, and into a breathing tube as shown in FIGS. 9 and 10. The channel 26 advantageously provides the device 2 the capability to receive MDCs with maximum diameters greater than the diameter of the chamber 12. The channel 26 allows two-way longitudinal movement (i.e., in to and out of) through the chamber 12 for MDCs having structures that radially extend beyond the diameter of the device 2, ultimately permitting engagement between the valve stem and the conduit well (i.e., enabling arrival of the valve stem to the conduit well).

In an embodiment, the profile of the channel 26 matingly receives the counter window. This "hand-in-glove" fit between the channel 26 and counter window 56 when the CoMDC is fully actuated permits the CoMDC 50 to be inserted into the chamber 12, correspondingly enabling the valve stem 60 to engage the conduit well 20.

In an embodiment the device 2 includes the CoMDC 50. FIGS. 6-10 will now be used to describe the loading of the CoMDC 50 in the device 2. FIGS. 6A, 6B show the CoMDC 50 separate from the device 2 prior to insertion. In FIG. 7, the CoMDC 50 is initially inserted into the top of the device 2. The CoMDC 50 is invertingly inserted such that the top 51 of the CoMDC 50 is the first portion of the CoMDC inserted into the chamber 12. As shown in FIG. 7, the counter window 56 is aligned with the channel 26. The counter window 56 moves freely, longitudinally along the channel 26. This permits insertion of the CoMDC 50 into the chamber 12. The channel 26 provides an opening for structure that extends beyond the diameter of chamber 12 (such as the counter window) which correspondingly enables the inverted CoMDC 50 to enter the chamber 12 of the body 4 and deliver the valve stem 60 to the well 20 of the conduit 16. As shown in FIGS. 8-10, the CoMDC 50 is generally centrally positioned within the chamber 12 and the counter window 56 is aligned between the opposing exposed edges 14a and 14b which facilitates engagement between the valve stem 60 and the conduit well 20. Depression of the (inverted) CoMDC bottom 53 (down arrow in FIG. 10) reciprocally engages the valve stem 60 to the well 20 and dispenses a metered dose of aerosolized medicament 84 into and through the conduit 16 out the discharge port 24, and into a breathing tube.

In an embodiment, a gap G is present between the (inverted) top 51 of the CoMDC 50 and the floor 8, when the CoMDC 50 is in the engagement position (as shown in FIG. 9). In the engagement position (uncompressed)—i.e., when the valve stem 60 is engaged with the conduit well 20 but before dispensing medicament—the gap G has a length from about 6 mm to about 12 mm. In the discharge position (valve stem 60 reciprocally engaged with well 20 to dispense medicament), the gap G may or may not be present between the inverted top 51 and the floor 8 as shown in FIG. 10. The act of depressing the bottom 53 of the CoMDC relative to the device 2 dispenses medicament and may (temporarily) shorten the length of (or eliminate) the gap G during dispensing of medicament. When the CoMDC is in the actuation position (compressed), the gap G has a length from 0 mm to about 8 mm, or from about 3 mm to about 6 mm. The act of depressing the bottom 53 also increments the counter—"47" in FIG. 9 moves to "46" in FIG. 10 indicating the number of doses remaining. It is noted also that during dispensing the top rim 6 has sufficient radial width so that finger(s) placed under the rim and a thumb on the CoMDC bottom can reciprocally move the valve stem 60 to discharge medicament through the conduit 16 and out the discharge port 24.

In an embodiment, the device 2 is configured for one-way insertion of the CoMDC 50 into the device 2. In other words, the device 2 provides a single insertion configuration or a sole load configuration for the inverted CoMDC 50. The channel 26 guides the inverted CoMDC 50 such that the only way insertion can proceed is by aligning the counter window 56 between the opposing exposed edges 14a and 14b in a "key-in-lock manner." The channel 26 thereby positions or orients the counter opening 62 on the top of the housing 54 (which is the first to enter the chamber) directly above the counter actuator 40 for male-female engagement of the counter actuator 40 with the counter device within the housing 54. Thus, the channel 26 functions as a guideway and ensures "one-way only load" or a single load configuration for the CoMDC 50. The device 2 advantageously (i) prevents false loads, (ii) permits a single (and proper) interface between the counter actuator and the counter device to ensure accurate tracking of the number of administered doses, (iii) avoids confusion by health care providers as how to load the CoMDC into the adaptor, and (iv) saves time when administering the medicament—which is especially advantageous when the medicament is administered in a life threatening situation where time is of the essence.

In an embodiment, a perforation 41 is present between the bottom of a removable actuator post 40a and the floor 8, as shown in FIGS. 11A-11D. The removable actuator post 40a is releasably attached or is otherwise removable from the floor 8 along the perforation 41. In this way, the actuator post 40a is removable from the device 2.

Figure 11A:
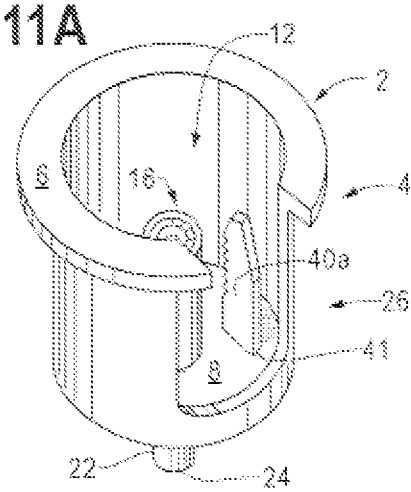
FIG. 11A is a perspective view of a device in accordance with an embodiment of the present disclosure.
Figure 11B:
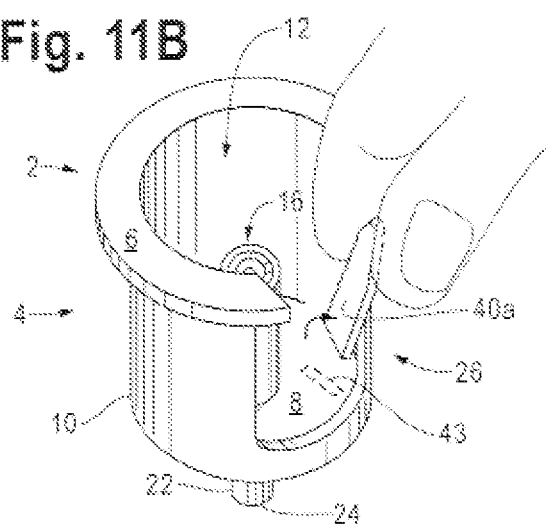
FIG. 11B is perspective view of a removable counter actuator being removed from the device of FIG. 11A in accordance with an embodiment of the present disclosure.
Figure 11C:
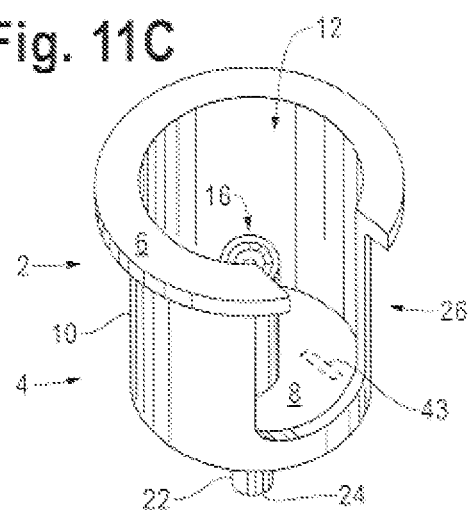
FIG. 11C is a perspective view of the device of FIG. 11A with a removable counter actuator removed therefrom in accordance with an embodiment of the present disclosure.

Fingers may be inserted into the chamber 12 to grasp the removable counter actuator 40a. It is understood that a small tool (tweezers, pliers, or other small device) may also be used to remove the removable counter actuator 40a. The removable counter actuator 40a is pulled, bent and/or snapped to break the perforation 41 and separate the removable counter actuator 40*a* from the floor 8. The removable counter actuator 40*a* is then removed from the chamber 12, as shown in FIGS. 11B and 11C. A score surface 43 remains where the removable counter actuator 40*a* once stood. The score surface 43 may or may not be flush with the floor 8. The channel 26 enables ready or easy removal of the removable counter actuator 40*a* by providing finger access to the removable counter actuator 40*a*.

Figure 11D:
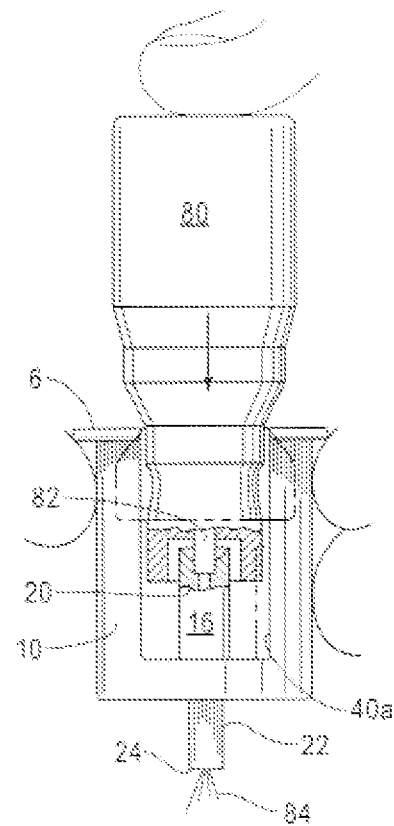
FIG. 11D is a front elevational view (and partial sectional view) of a metered dose canister in the device of FIG. 11C in accordance with an embodiment of the present disclosure.

FIG. 11D shows an C-MDC 81 inserted in the chamber 12 with a valve stem 82 being actuated (reciprocal engagement with the well 20) to dispense an aerosolized spray of medicament 84 through the discharge port 24. Phantom lines in FIG. 11D show where the removable counter actuator 40*a* once stood. Although FIG. 11D indicates reference numeral 40*a*, it is understood that 40*a* in FIG. 11D indicates the phantom lines where the removable counter actuator stood and would have interfered with a structure 83 of the inverted C-MDC 81. A non-limiting example of structure 83 is a housing. By removing the removable counter actuator 40*a*, no interference occurs and the C-MDC 81 operates unobstructed to deliver the aerosolized spray of medicament.

The present disclosure provides another device. In an embodiment, a device (or adaptor) 202 for delivering a medicament from a MDC/C-MDC/CoMDC into a breathing tube is provided as shown in FIGS. 14-20. The device 202 includes a body 204, a flange 276, a floor 208, and a sidewall 210. The sidewall 210 is arcuate and extends between the flange 276 and the floor 208 and provides the body 204 with a substantially cylindrical, or cylindrical, shape. The body 204 defines a substantially cylindrical, or cylindrical, chamber 212. The chamber 212 is adapted to receive an inverted MDC (or inverted C-MDC), or an inverted CoMDC, as will be discussed below. The sidewall includes opposing exposed edges 214*a*, 214*b*. The device 202 also includes a conduit 216.

Figure 15:
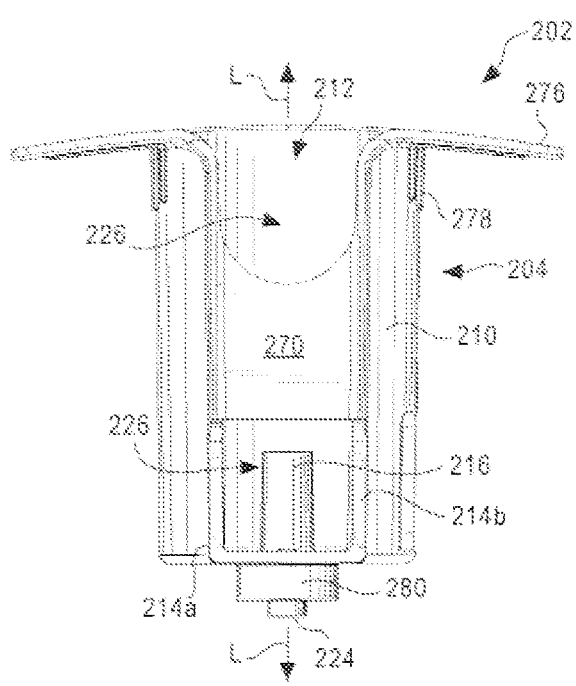
FIG. 15 is a front elevation view of the device of FIG. 14 in accordance with an embodiment of the present disclosure.
Figure 21A:
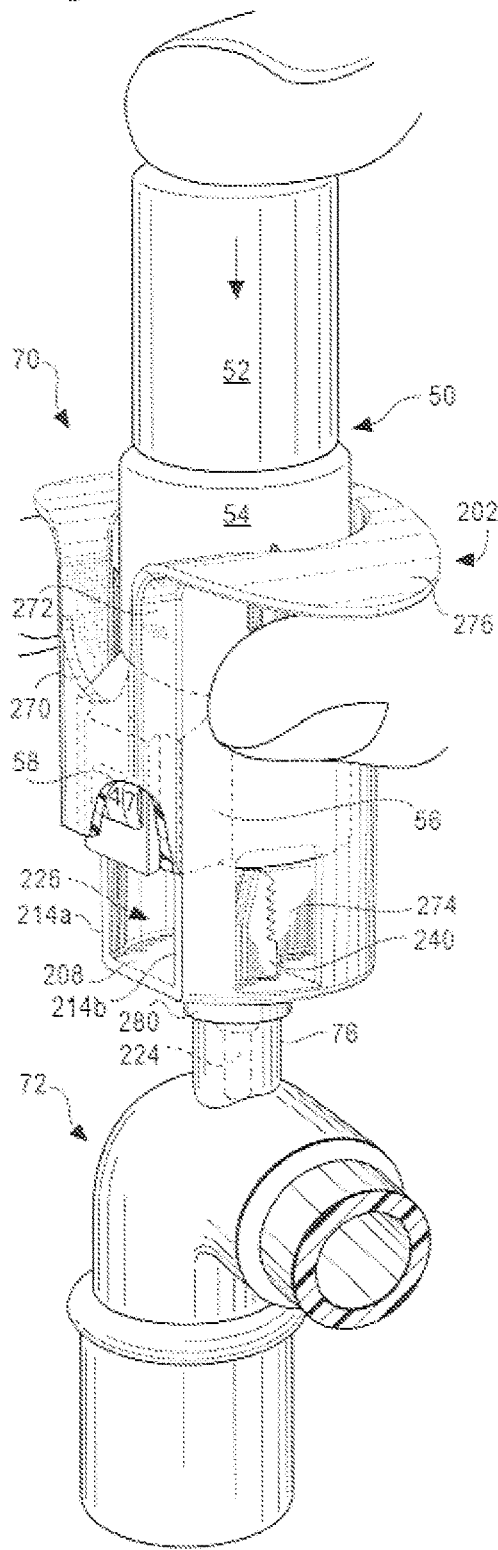
FIG. 21A is a perspective view of an assembly in accordance with an embodiment of the present disclosure.

As shown in FIG. 15, the conduit 216 is annular and extends from the chamber 212, through the floor 208, and below the floor 208. The conduit 216 vertically extends from the chamber 212, through the floor 208 and vertically below the floor 208. The conduit 216 is centrally located in chamber 212 as shown in FIGS. 15 and 19. A well 220 is located at an upper portion of the conduit 216. The well 220 is located within the conduit 216 and is adapted to receive or otherwise engage the valve stem of an inverted MDC/C-MDC/CoMDC, as will be described below. Below the floor 208, the conduit 216 includes a discharge port 224 which is vertically disposed below the floor 208. The discharge port 224 is surrounded by a band 280 that is integral to the floor 208 and extends downward from the floor 208. The band 280 includes structure (see FIG. 20) to form a fluid-tight Luer seal with a Luer port located on a receiving structure (FIG. 21A). The discharge port 224 is configured to dispense aerosolized medicament. The conduit 216, the well 220, and discharge port 224 are configured to receive aerosolized medicament expelled from a valve stem of an MDC/C-MDC/CoMDC and convey or otherwise deliver the aerosolized medicament into a breathing tube and into an intubated patient.

The sidewall 210 includes exposed edge 214*a* and exposed edge 214*b* in opposing relation to each other. Opposing exposed edges 214*a*, 214*b* extend from the top of the body 204, and extend longitudinally downward to, or substantially to, the floor 208. Exposed edge 214*a* opposes exposed edge 214*b* as shown in FIG. 15. Exposed edge 214*a* is parallel to, or substantially parallel to, exposed edge 214*b*.

Figure 14:
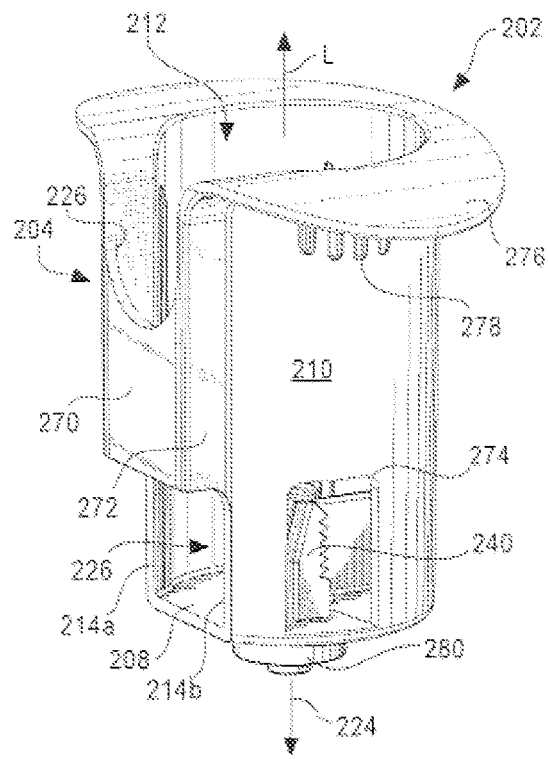
FIG. 14 is a perspective view of a device in accordance with an embodiment of the present disclosure.

Similar to opposing exposed edges 14*a*, 14*b* and channel 26 of device 2, in device 202, the opposing exposed edges 214*a*, 214*b* define a channel 226 in the sidewall 210 as shown in FIGS. 14-15. The channel 226 permits longitudinal passage or longitudinal travel of a counter window as an inverted CoMDC is loaded into the chamber 212 as will be described below. The counter window longitudinally moves along the channel 226 as the valve stem of the inverted CoMDC moves into engagement with the conduit well. Longitudinal movement is movement along and/or parallel to, or substantially parallel to, longitudinal axis L.

Similar to device 2, the dimensions of the opposed exposed edges 214*a*, 214*b* and the resultant channel 226 of device 202 may be varied so that device 202 can receive an MDC/C-MDC/CoMDC of various shapes and/or dimensions. In an embodiment, the opposing exposed edges may extend from the flange 276 all the way to the floor 208 as shown in FIGS. 14-15.

As shown in FIGS. 14-20, the device 202 includes a bridge 270 extending between the opposing exposed edges 214*a*, 214*b*. The bridge 270 extends between and connects exposed edge 214*a* to exposed edge 214*b*. The bridge 270 may be releasably attached or permanently attached to exposed edge 214*a* and/or exposed edge 214*b* and/or the sidewall 210. In an embodiment the bridge 270 is permanently attached to each exposed edge 214*a* and 214*b*.

In an embodiment, the bridge 270 has a top arcuate edge and a bottom edge. The distance between the top arcuate edge and bottom edge of the bridge is such that when the valve stem 60 is engaged with the well 220 of the conduit 216, the bridge 270 does not obstruct the view of the counter window 56 when the device 202 is loaded with the CoMDC 50.

Figure 16:
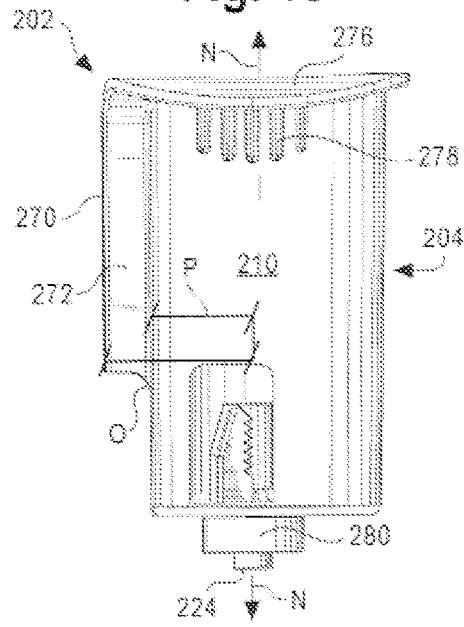
FIG. 16 is a left elevation of the device of FIG. 14 in accordance with an embodiment of the present disclosure.
Figure 17:
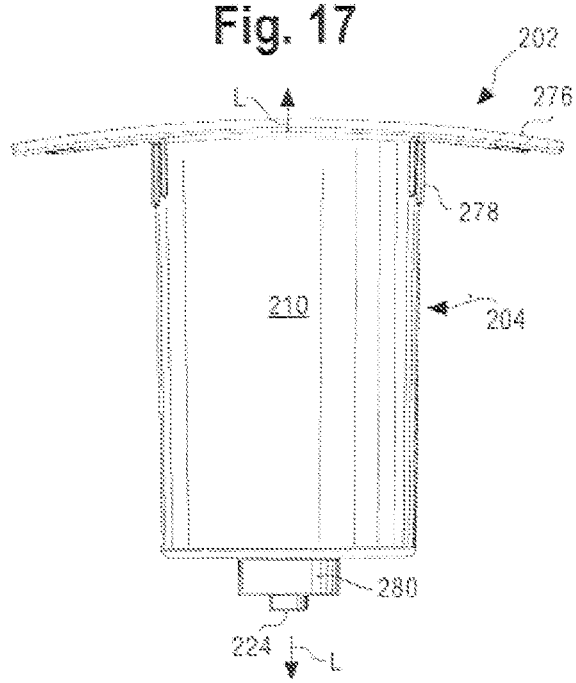
FIG. 17 is a rear elevation view of the device of FIG. 14 in accordance with an embodiment of the present disclosure.

In an embodiment, legs 272 connect the bridge 270 to the opposing exposed edges 214*a*, 214*b*. The legs 272 place the bridge 270 radially outward with respect to the body 204. This is best seen in FIG. 16 where length O, the distance between center axis N and the bridge 270, is greater than the length P, the distance between the center axis N and the radial extent of the sidewall 210.

FIG. 14 shows the bridge 270 extending between legs 272 that extend radially outward from the channel 226. The legs 272 have a length which provides a radial space between an MDC/C-MDC/CoMDC loaded into the chamber 212. In this way, the legs 272 permit unobstructed longitudinal movement between an MDC/C-MDC/CoMDC and the underside (radially inward side) of the bridge 270. For example, when the CoMDC 50 is invertedly loaded into the chamber 212 of the device 202, the counter window 56 moves freely between the opposing exposed edges 214*a*, 214*b*. The counter window 56 also moves unobstructed under the bridge 270 permitting reciprocal engagement between the valve stem 60 and the well 220 for discharge of a medicament puff through the conduit 216 and expelled through the discharge port 224.

Provision of the bridge 270 advantageously permits easier molding and manufacturing of device 202. The bridge 270 provides additional structural support of device 202 thereby increasing the overall strength and durability of device 202.

In an embodiment, the sidewall 210 of device 202 has an opening 274 that allows access to a counter actuator 240. The counter actuator 240 may be a removable counter actuator and/or a bendable counter actuator. The term "access," or "accessible," as used herein, includes viewing, inspecting, moving, bending, and/or removing the counter actuator 240. The opening 274 may be any shape, including rectangular, circular, oblong, trapezoidal, among others. Fingers and/or suitable instruments may be inserted through the opening 274 to access the counter actuator 240.

Device 202 includes the flange 276. The flange 276 extends radially outward from the longitudinal axis L. The flange 276 advantageously improves the handling and the operation of the device 202, especially when administering medicament. On the bottom side of the flange 276 are raised ridges 278 that extend partially down the sidewall 210. The raised ridges 278 also aid in handling device 202 by providing additional grip and/or traction for the user handling the device 202.

Nonlimiting dimensions for the following components of the device 202 are provided in Table 2 below.

TABLE 2

| Component | Dimension (millimeter) |
| --- | --- |
| Body 204 (including port 224) | Longitudinal length: 30-60 or 50 |
| Flange 276 (greatest diameter) | Flange tip to flange tip: 55-65, or 58 |
| Floor 208 | Thickness: 0.1-2, or 1 |
| Sidewall 210 | Longitudinal length |
|  | Inner 40-50, or 43 |
|  | Outer 40-50, or 46 |
| Chamber 212 | Diameter: 20-30, or 24 |
| Exposed edge 214a, 214b | Longitudinal length: 10-20, or 14 |
| Conduit 216 | Longitudinal length: (with port 224) 10-20, or 16 |
|  | Outer diameter: 4-8, or 5 |
| Well 220 | Inner diameter: 2-4, or 3 |
| Channel 226 | Width: 10-18, or 13 |
| Bridge 270 | Width 15-20, or 17 |
|  | Length (longitudinal) 25-30, or 28 |
| Legs 272 | 3-8, or 5 |
| Gap M - Distance Between Bridge 270 and Counter Window 56 | 0-3 or 1 |

The present device 2, 202 thereby provides a universal adaptor for many different types of MDCs. The present device 2, 202 can receive, accommodate, or otherwise operatively communicate with a CoMDC as previously discussed. The present device can also operatively communicate with a C-MDC. The present device can also operatively communicate with a MDC that is, or is not, compatible with the removable counter actuator 40a. In the event the removable counter actuator interferes with the insertion and/or the actuation of an MDC, the removable counter actuator 40a, 240 can be removed providing unobstructed longitudinal movement of the MDC in the device 2, 202 for actuation.

The device 2, 202 may be made of metal, glass, a polymeric material, and combinations thereof. Nonlimiting examples of suitable metals include aluminum, anodized aluminum, brass, carbon steel, chrome plated brass, chrome plated steel, copper, nickel, nickel silver alloy, stainless steel, steel, titanium, tungsten carbide, and any combination thereof. Nonlimiting examples of suitable polymeric material include propylene-based polymer, ethylene-based polymer, polymethylmethacrylate (acrylic), polyamide (nylon), polyethylene terephthalate, polystyrene, polyvinylchloride, acrylonitrile/butadiene/styrene (ABS), polysulfone, polycarbonate, acetal PTFE, polychloroprene (Neoprene), Kraton G, polyurethane, rubber, silicone rubber, latex, and combinations thereof.

The device 2, 202 has many advantages. The device 2, 202 is versatile and can deliver aerosolized medicament from a MDC a C-MDC or a CoMDC. Provision of the conduit upper portion 18, 218 advantageously enables the device 2, 202 to receive the valve stem of an MDC as well an embedded valve stem, as found in C-MDCs and/or CoMDCs. The chamber 12, 212 provides suitable space around the conduit upper portion 18, 218 to accommodate the housing of a C-MDC while the sidewall 10, 210 simultaneously provides suitable longitudinal support for an MDC to prevent false dosing, valve stem binding, tipping and/or damage to the valve stem. The device 2, 202 also provides adequate spacing between the floor 8, 208 and the well 20, 220 such that an MDC can be fully actuated.

The present adaptor has the versatility to discharge medicament from an MDC, a C-MDC as well as from a CoMDC. It is understood that MDCs do not have a counter window, but may have other structures that extend radially outwardly beyond the diameter of the adaptor chamber. The channel 26, 226 is adapted to allow extension of such a structure radially beyond the adaptor chamber as previously discussed. In addition, the channel is sized such that the sidewall substantially surrounds the container of the MDC to thereby align the MDC within the chamber 12, 212. This ensures that the MDC will not fall out of, or tip out of, the adaptor.

The present device (adaptor) may comprise two or more embodiments disclosed herein.

In an embodiment, an assembly 70 is provided for delivering medicament from a multi-dose canister (MDC) as shown in FIGS. 12A-12C and a counter metered-dose canister (CoMDC) in FIGS. 21A-21C. The MDC includes a valve stem. The assembly 70 includes the device 2, 202 as previously disclosed herein. The following reference numerals shown in parenthesis refer to device 202. In particular, the device 2, 202 includes the substantially cylindrical body 4, (204), with the top rim 6, (206) and floor 8, (208) and the arcuate sidewall 10, (210) extending therebetween. The body 4, (204) defines the chamber 12, (212), which is adapted to receive an inverted MDC. The device 2, 202 also includes the conduit 16, (216) extending from the chamber 12, (212) through the floor 8, (208). The conduit 16, 216 has the well 20, (220) located within the chamber 12, (212). The well 20, (220) is adapted to engage the valve stem. The conduit 16 (216) includes the discharge port 24, (224) disposed below the floor 8, (208) for dispensing medicament. The arcuate sidewall 10, (210) includes the opposing exposed edges 14*a*, 14*b*, (214*a*, 214*b*) which define the channel 26, (226) extending longitudinally from the top rim 6, (206) substantially to the floor 8, (208). Device 202 further includes bridge 270, optional legs 272, flange 276, raised ridges 278, opening 274 in the sidewall 210, and band 280 surrounding the discharge port 224.

The assembly 70 also includes a breathing tube connector having an inlet. The inlet is in fluid communication with the discharge port 24, (224). The inlet receives medicament from the conduit 16, (216) dispensed from the inverted MDC.

The breathing tube connector may be integral to a breathing tube—i.e., the breathing tube connector may be a breathing tube. Alternatively, the breathing tube connector may be a distinct or a separate component that is placed in operative communication, or in fluid communication, with a breathing tube. In other words, the device 2, 202 may be in fluid communication with an inlet that is an element of a breathing tube (direct connection to breathing tube) or may be in fluid communication with an inlet of a structure that is connected to a breathing tube (indirect connection to breathing tube). The breathing tube connector may be made of metal, glass, polymeric material, or combinations thereof as previously disclosed herein.

In an embodiment, the assembly 70 includes a breathing tube connector 72. The breathing tube connector 72 is a separate component and is connected to a breathing tube 74 as shown in FIGS. 12A-12C, FIG. 13, and FIGS. 21A-21C.

The breathing tube connector 72 is an elbow shaped connector. Although an elbow-shaped connector is shown, other configurations for the breathing tube connector are also possible. Nonlimiting examples of other suitable breathing tube connectors include Y-tube connectors, T-tube connectors, branched connectors, and straight line connectors. It is understood that the device 2 may be connected to any type of breathing tube as well as one or more of such tubes. Non-limiting examples of breathing tubes include an endotracheal tube, a nasotracheal tube, and a tracheal tube (and intubation tubes and/or stoma insertion tubes). The breathing tube(s) is typically one part of an intubation system or breathing circuit which includes a monitoring device 78 for administering gases to the patient and/or monitoring breathing/heart, or other vital signs of the intubated patient.

The breathing tube connector 72 includes an inlet 76. The discharge port 24, (224) is in fluid communication with the inlet 76. The conduit lower portion 22 (which may be 22a or 22b) engages the inlet 76 to form a male-female connection that is leak-free, or substantially leak-free or otherwise air-tight (or substantially air-tight). The inlet 76 may be raised (outwardly extending from the breathing tube connector), depressed (inwardly extending into the inner passageway of the breathing tube connector), or flush with the outer surface of the breathing tube connector 72. In an embodiment, the engagement between the conduit lower portion 22, (224) and the inlet 76 is a frictional engagement. In another embodiment, a threaded engagement provides communication between the conduit lower portion 22, (224) and the inlet 76 whereby the threads on the conduit lower portion are screwed into reciprocal threads present on the inlet 76.

In an embodiment, the inlet 76 is a Luer port. A "Luer port" (which includes "Luer fitting," "Luer lock," "Luer slip," and/or "Luer locking ring") is a leak-free connection between a male annular component and a female annular component by way of frictional engagement and/or threaded engagement. A Luer port may or may not include a conical fit or a tapered fit between the male component and the female component.

Figure 12A:
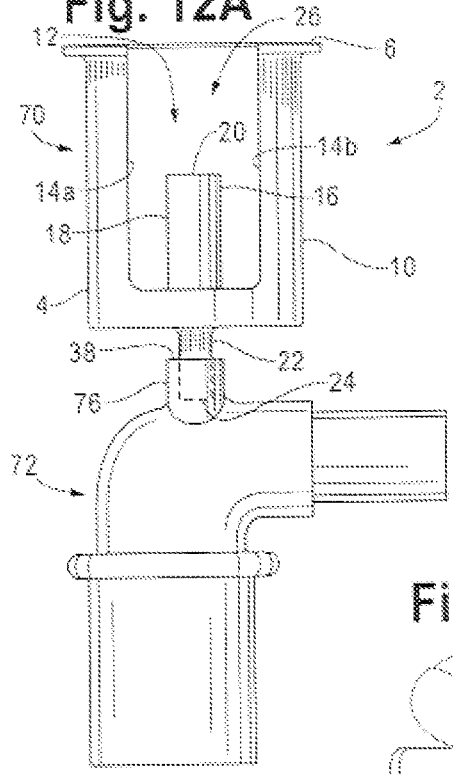
FIG. 12A is a front elevation view of an assembly in accordance with an embodiment of the present disclosure.

FIG. 12A and FIG. 21A show embodiments wherein the discharge port 24, (224) is inserted into the inlet 76 and is received in a frictional fit. The frictional fit provides a fluid-tight connection between the discharge port 24, (224) and the inlet 76. In FIG. 12A, the inner diameter of the inlet 76 and the outer diameter of the discharge port 24, (224) are sized to achieve a suitable friction fit. In an embodiment, the collar 38 provides a stop for insertion.

In an embodiment the band 280 of device 202 has structure to form a fluid-tight Luer seal with the inlet 76 (FIGS. 20, 21A).

Figure 12B:
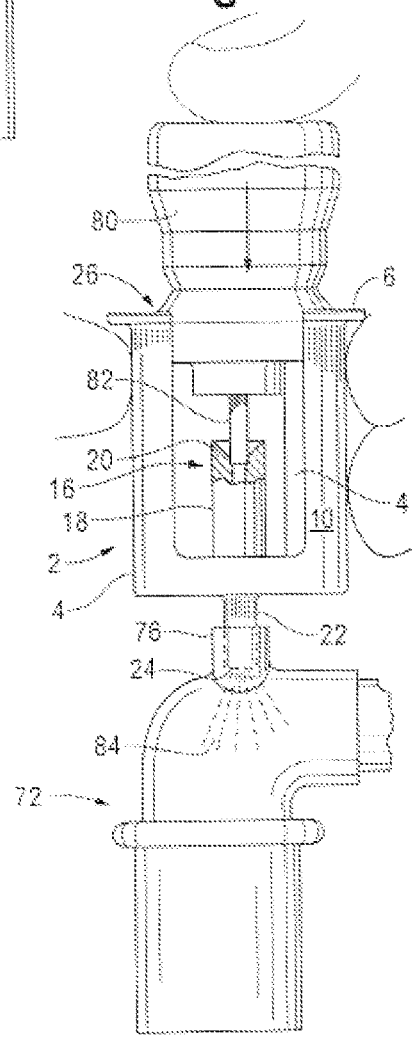
FIG. 12B is a front elevation view (and partial sectional view) of an assembly in accordance with an embodiment of the present disclosure.
Figure 12C:
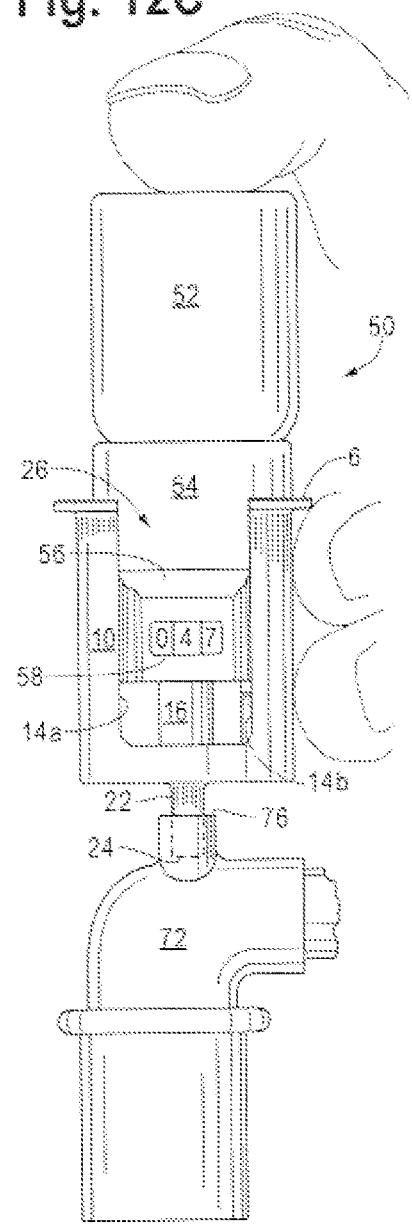
FIG. 12C is a front elevation view of an assembly in accordance with an embodiment of the present disclosure.

In an embodiment, the assembly 70 includes an MDC 80. FIG. 12B illustrates the insertion of the MDC 80 into the adaptor 2, 202. The MDC 80 has a valve stem 82 that is received by the conduit well 20. The MDC 80 is inverted and inserted in the chamber 12 where the conduit well 20 reciprocally engages the valve stem 82. The bottom of the MDC 80 is depressed (down arrow in FIG. 12B) to actuate the MDC 80 and dispense a metered dose of aerosolized medicament 84 through the conduit 16, through the discharge port 24, through the inlet 76 and into the breathing tube connector 72. As shown in FIG. 12B, a gap H is present between the (inverted) top of the MDC 80 and the floor 8 of the device 2. In the engagement position (uncompressed), the gap H has a length from about 18 mm to about 22 mm (uncompressed). In the actuation position (compressed), the gap H has a length from about 16 mm to about 20 mm.

In a further embodiment, the assembly 70 includes the CoMDC 50 as shown in FIG. 12C and FIGS. 21A-21C. The device 2, 202 receives the CoMDC 50 as previously disclosed herein. This illustrates the versatility of the present device 2, 202 which can operatively receive a MDC or a CoMDC (as well as a C-MDC) and dispense, from either, an aerosolized medicament into a breathing tube and/or a breathing tube connector and into the lungs of an intubated patient.

Figure 21B:
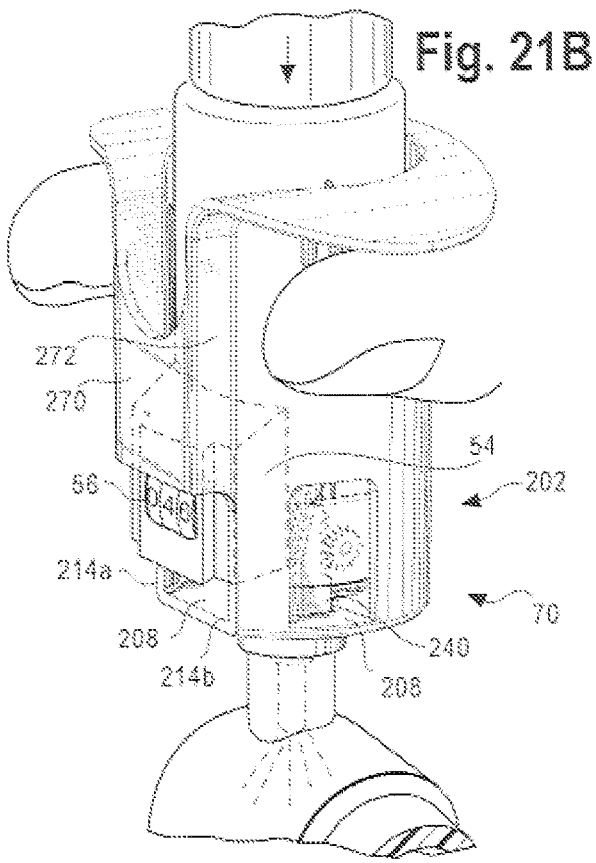
FIG. 21B is a perspective view of an assembly in accordance with an embodiment of the present disclosure.

FIGS. 21A and 21B show assembly 70 including the device 202 with CoMDC 50 loaded therein and the device 202 in fluid communication with the breathing tube connector 72. Fingers are placed under the flange 276. As the CoMDC 50 is pressed downward (shown by downward arrow in FIGS. 21A, 21B) by a person's thumb, the counter actuator 240 enters the counter opening 62. The counter window 56 moves or otherwise slides between the opposing exposed edges 214a, 214b. The counter window 56 and a portion of the housing 54 are shown in phantom in FIGS. 21A and 21B. As downward movement of the inverted CoMDC 50 continues, the counter window 56 moves freely under the bridge 270. In other words, the counter window 56 moves unobstructed along the underside of the bridge 270. Contact may occur between the underside of the bridge 270 and the counter window 56. The downward force from the person's thumb is sufficient to overcome any friction between the underside of the bridge 270 and the counter window 56.

The downward pressure (shown by the downward arrow) on the inverted CoMDC 50 in the chamber 212 proceeds as shown in FIG. 21B. The valve stem 60 reciprocally engages the well 220 (not shown) to discharge a puff of aerosolized medicament through the conduit 216, through the discharge port 224 and into the breathing tube 72. A COG (phantom) in the housing 54 engages the counter actuator 240 (partial phantom) to increment the counter from "47" doses remaining to "46" doses remaining.

Figure 21C:
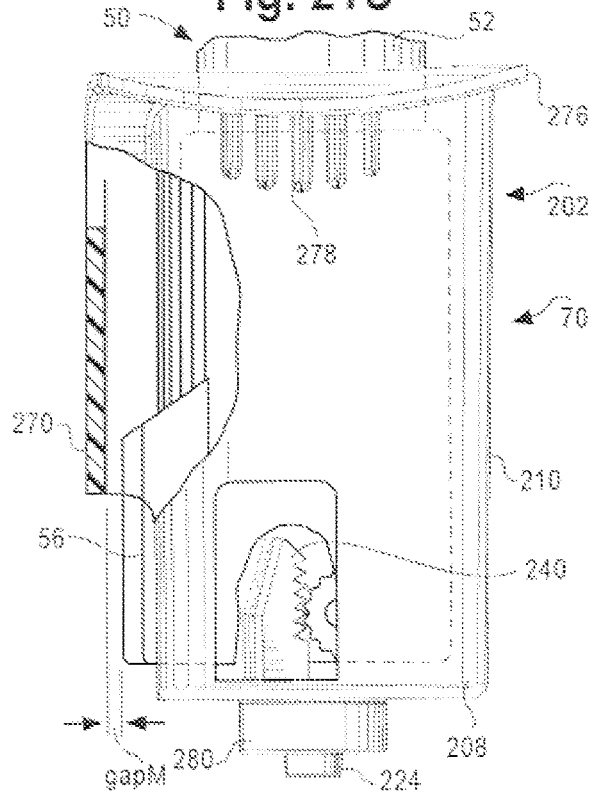
FIG. 21C is a side view of an assembly in accordance with an embodiment of the present disclosure.

FIG. 21C shows the inverted CoMDC 50 after medicament discharge and in the fully depressed position in the device 202. The gap M is the distance between the underside of the bridge 270 and the counter window 56. The gap M can have a length from 0 mm, or greater than 0 mm, or 0.1 mm, or 0.2 mm, or 0.3 mm, or 0.4 mm, or 0.5 mm to 5 mm, or 4 mm, or 3 mm, or 2 mm, or 1 mm.

The assembly may comprise two or more embodiments disclosed herein.

The present disclosure provides a system and/or a method. In an embodiment, a method for administering medicament from a multi-dose canister (MDC) (or a C-MDC, or a CoMDC) to an intubated patient is provided. The method includes invertingly inserting an MDC into the device 2 or the device 202 as previously disclosed herein. The following reference numerals shown in parenthesis refer to device 202. The device 2, 202 includes the following components as disclosed above: body 4, (204), top rim 6, (flange 276), floor 8, (208), arcuate sidewall 10, (210), chamber 12, (212), opposing exposed edges 14a, 14b, (214a, 214b), conduit 16, (216), a well 20, (220), discharge port 24, (224), and channel 26, (226), The MDC may be MDC 80 including a container and a valve stem as previously disclosed herein. The device 202 also includes the bridge 270, legs 272, and flange 276.

The method includes placing the discharge port in fluid communication with an inlet of a breathing tube. The fluid communication may be any communication and/or engagement between the device and the inlet as previously disclosed herein. The method includes reciprocally engaging the valve stem with the conduit well. This expels a metered dose of aerosolized medicament from the MDC into the conduit. The method includes dispensing the medicament from the MDC through the conduit and into the breathing tube. In an embodiment, the method includes delivering, through the breathing tube, the medicament to the intubated patient (to the lungs of the intubated patient). The breathing tube may be any breathing tube or breathing tube connector as previously disclosed herein.

In an embodiment, the method includes placing at least one finger (or two fingers) under the top rim 6, depressing the bottom of the inverted MDC with another finger (such as the thumb) to reciprocally engage the valve stem with the conduit well and administer a metered dose of aerosolized medicament to the intubated patient (as shown in FIGS. 12B, 13 and 13A). It is also possible to hold the device 2 with the thumb and middle finger and depress the MDC with the index finger.

In an embodiment, the MDC is a CoMDC as previously disclosed herein. The method includes guiding, with the opposing exposed edges 14a, 14b, the counter window 56 of the CoMDC 50 along the channel 26. The method may also include longitudinally moving the counter window 56 along the channel 26. The method may also include extending at least a portion of the counter window 56 radially outwardly through and beyond the body 4 and longitudinally moving the CoMDC into the chamber 12. This permits the reciprocal engagement between the valve stem 60 with the conduit well 20 as previously disclosed. It is understood that other radially outwardly extending structure of a MDC may be extended through the channel enabling longitudinal movement of MDC into the chamber in a similar manner.

In an embodiment, the method includes displaying the counter window 56 through the channel 26.

The method further includes dispensing medicament from the MDC (or CoMDC) through the conduit 16, through the breathing tube, and to the intubated patient 90. FIG. 13A is an enlarged sectional view of area 13A of FIG. 13. FIGS. 13 and 13A show aerosolized medicament 84 dispensing from the CoMDC 50 through the conduit 16 through the inlet 76 into the breathing tube connector 72. The resulting spray is delivered through the breathing tube 74 and into the intubated patient 90. As shown in FIGS. 9, 10, 12, 12A, 13, and 13A, the user dispenses the medicament by pressing the bottom or canister end with a thumb and uses the forefinger and middle finger to hold the underside of the top rim on either side of the device.

In an embodiment, a method for administering medicament from a counter metered-dose canister (CoMDC) in to an intubated patient is provided. The method includes invertingly inserting an MDC into the device 202. The device 202 includes the following components as disclosed above: body 204, top rim 206, floor 208, arcuate sidewall 210, chamber 212, opposing exposed edges 214a, 214b, conduit 216, a well 220, discharge port 224, and channel 226. The MDC may be CoMDC 50 including a container and a valve stem as previously disclosed herein.

The method includes placing the discharge port 224 in fluid communication with an inlet of a breathing tube. The fluid communication may be any communication and/or engagement between the device and the inlet as previously disclosed herein. The method includes reciprocally engaging the valve stem 60 with the conduit well 220. This expels a metered dose of aerosolized medicament from the CoMDC into the conduit 216. The method includes dispensing the medicament from the CoMDC through the conduit and into the breathing tube 72. In an embodiment, the method includes delivering, through the breathing tube, the medicament to the intubated patient (to the lungs of the intubated patient). The breathing tube may be any breathing tube or breathing tube connector as previously disclosed herein.

In an embodiment, the method includes placing at least one finger (or two fingers) under the flange 276, depressing the bottom of the inverted CoMDC 50 with another finger (such as the thumb) to reciprocally engage the valve stem with the conduit well and administer a metered dose of aerosolized medicament to the intubated patient (as shown in FIGS. 21A-21C). It is also possible to hold the device 202 with the thumb and middle finger and depress the CoMDC with the index finger.

The method includes guiding, with the opposing exposed edges 214a, 214b, the counter window 56 of the CoMDC 50 along the channel 226. The method also includes longitudinally moving the counter window 56 along the channel 226. The method also includes extending at least a portion of the counter window 56 radially outwardly through and beyond the body 204 and longitudinally moving the CoMDC into the chamber 212. This permits the reciprocal engagement between the valve stem 60 with the conduit well 220 as previously disclosed. It is understood that other radially outwardly extending structure of a CoMDC may be extended through the channel 226 enabling longitudinal movement of CoMDC into the chamber in a similar manner.

In an embodiment, as shown in FIGS. 21A-21C, the method includes longitudinally moving CoMDC 50 into chamber 212, passing the counter window 56 under the bridge 270. The counter window 56 moves freely under the bridge 270. In other words, the bridge 270 does not obstruct the movement of the counter window 56 through the channel 226. FIG. 21A shows the counter 58 indicating 47 doses remaining and once the medicament is administered, FIG. 21B shows the counter 58 indicating 46 doses remaining. Device 202 may be configured such that the bridge 270 does not obstruct the view of the counter window 56 once the valve system 60 is engaged with the conduit well 220, as shown in FIG. 21B.

In an embodiment, the device 2, includes the counter actuator 40. The method includes inserting the counter actuator 40 into the counter opening 62 and incrementing the counter of the CoMDC 50 with the counter actuator 40.

In an embodiment, the device 2 includes the removable counter actuator 40a. The method includes removing the removable counter actuator 40a (along perforation 41) from the chamber and reciprocally engaging the value stem with the conduit well.

In an embodiment, the method utilizes device 202 and includes removing the counter actuator 240 by way of the opening 274 in the sidewall 210 that allows access to the counter actuator 240. In another embodiment, the method utilizes device 202 and includes bending the counter actuator 240 to allow engagement of the valve stem 60 with the conduit well 220. Removal or bending of the counter actuator 240 occurs in the event the counter actuator 240 obstructs or otherwise prevents the reciprocal engagement between the valve stem 60 and the well 220.

In an embodiment, the intubated patient indicates a breathing problem. The method includes delivering the medicament (with the present device 2 or 202) to the intubated patient and alleviating the breathing problem. The medicament may be any medicament as previously disclosed herein. In a further embodiment, the method includes administering albuterol (and/or ipatroprium) to an intubated patient indicating the breathing problem and alleviating the breathing problem. A nonlimiting example of a breathing problem is an asthma attack. The method further includes administering albuterol and alleviating an intubated patient having an asthma attack.

In an embodiment, the method includes loading an MDC (or C-MDC or CoMDC) into the chamber of the present device, inserting the device into an inlet, of a breathing tube (or breathing tube connector) and actuating the MDC to administer aerosolized medicament in a time duration from about three seconds to less than eight seconds, or from about three seconds to less than five seconds. The present device advantageously provides rapid load of the MDC and discharge of medicament to an intubated patient in less than eight seconds, or less than five seconds.

The method may comprise two or more embodiments disclosed herein.

In an embodiment, the device 2, 202, is a component of a system, such as a breathing (and/or anesthesia) circuit 100 as shown in FIGS. 13, 13A. The device 2, 202 advantageously allows the administration of aerosolized medicament without adding a significant volume of gas to the breathing circuit 100. For example, administering an aerosolized medicament by way of a conventional nebulizer is slow and expensive. A conventional nebulizer requires 3 to 5 liters of gas per minute to be added to the breathing circuit in order to deliver a dose of aerosolized medicament to the intubated patient. The present device 2, 202, adds a precise amount of aerosolized medicament directly to lungs of the intubated patient. In this way, use of the present device 2, 202, is advantageous as it does not dilute the anesthetic concentration in the breathing circuit.

The present device 2, 202 is advantageous compared to conventional adaptors. Conventional adaptors (such as the Bronchodilator Tee produced by Boehringer Labs, U.S. Pat. No. D294,298) or the like), or in-line adaptors for application of MD canisters (such those produced by VBM Medizintechnik GmbH of Germany, for example) require the breathing circuit to be opened in order to administer aerosolized medicament. In addition, circuit hoses and/or the endotracheal tube need to be re-connected with the adaptor before aerosolized medicament can be administered. Reconnection of the hoses/tubes takes time (at least 10 seconds or more), during which time anesthetic gas in the breathing circuit is lost to the ambient air resulting in contamination. Replacement of the hoses/tubes with a conventional adaptor also produces a substantial leak in the breathing circuit which reduces the breathing circuit pressure ("pressure drop") and interrupts ventilation. Some critically ill patients require constant airway pressure even during exhalation to maintain oxygenation. A sudden stop in ventilation and/or reduction in airway pressure to ambient pressure may worsen the patient's pulmonary condition.

The present device 2, 202 advantageously minimizes contamination, minimizes breathing circuit pressure drop, and/or minimizes ventilation interruption. As shown in FIGS. 13, 13A the present device is placed in operative communication with the breathing circuit 100 quickly (8 seconds or less, or 5 seconds or less) with little or no pressure drop, little or no contamination, and/or little or no ventilation interruption. Although FIGS. 13 and 13A show device 2, it is understood that system 100 can also include device 202. Insertion (and removal) of the discharge port 24 (224) into the breathing tube inlet (such as a Luer port) is simple, quick, does not require dis-/re-connection of hoses or tubes, and requires only a small break in the breathing circuit minimizing contamination, minimizing breathing circuit pressure drop, and minimizing ventilation interruption. In addition, the present device adds no "dead-space" to the breathing/anesthetic circuit. Use of the present device thereby avoids the risk of carbon dioxide accumulation (which can be a substantial risk, especially with intubated neonates, infants and children), a risk that is increased with the addition of in-line adaptors leading to increased dead space in conventional breathing circuits.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a property, such as, for example, length is from 100 to 1,000, then the intent is that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure.

The terms "comprising", "including", "having" and their derivatives are not intended to exclude the presence of any additional component, step or procedure, whether or not the same is specifically disclosed. In order to avoid any doubt, all compositions claimed through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

It is specifically intended that the present disclosure not be limited to the embodiments and illustrations contained herein, but include modified forms of those embodiments including portions of the embodiments and combinations of elements of different embodiments as come within the scope of the following claims.

The invention claimed is:

1. A device for delivering a medicament into a breathing tube from a counter metered-dose canister (CoMDC) comprising a valve stem and a counter window, the device excluding a boot-type inhaler comprising:
   a body defining a chamber adapted to receive an inverted CoMDC, the body comprising:
   a floor;
   an arcuate sidewall defining a chamber for receiving the CoMDC, a portion of the sidewall comprising opposing exposed edges defining a U-shaped profile free of sidewall;
   a vertical conduit extending from the chamber through the floor and into a breathing tube connector located below the floor, the vertical conduit having:
      an upper portion located in the body chamber,
      a well located above the floor and within the chamber for engagement with the valve stem of the inverted CoMDC; and a lower portion having a discharge port located in the breathing tube connector for dispensing medicament.

2. The device of claim 1 wherein the body is a single, integral piece of material.

3. The device of claim 1 wherein the device is adapted to receive a CoMDC with a maximum cross-sectional diameter greater than the diameter of the chamber.

4. The device of claim 1 wherein the channel provides a single load configuration for the inverted CoMDC.

5. The device of claim 1 wherein the opposing exposed edges are adapted to guide the counter window along the channel.

6. The device of claim 1 comprising a counter actuator extending upwardly from the floor for actuating a counter of the CoMDC when medicament is dispensed.

7. The device of claim 1 comprising an inverted CoMDC in the chamber and the counter window is located between the opposing exposed edges.

8. The device of claim 7 wherein at least a portion of the counter window extends radially outward through the channel and outside the chamber.

9. The device of claim 7 wherein the valve stem is reciprocally engaged with the conduit well.

10. The device of claim 1 wherein the opposing exposed edges extend downwardly from a top rim of the body to the floor.

11. The device of claim 1 wherein the conduit well is spaced upwardly from the floor and coaxial with a longitudinal axis of the body.

12. The device of claim 1 wherein the discharge port is coaxial with a longitudinal axis of the vertical conduit.

13. The device of claim 1 comprising a breathing tube connector comprising an inlet in fluid communication with the discharge port for receiving medicament dispensed from the CoMDC.

14. The device of claim 13 wherein the breathing tube connector is in fluid communication with an intubated patient.

15. The device of claim 13 wherein the breathing tube connector is a straight line connector.

16. A method for administering medicament from a counter metered-dose canister (CoMDC) to an intubated patient, the method comprising:
   invertingly inserting the CoMDC into a device comprising,
   a body comprising a top rim, a floor, and an arcuate sidewall therebetween defining a chamber for receiving the inverted CoMDC, a portion of the sidewall comprising opposing exposed edges defining a U-shaped profile free of sidewall, a vertical conduit extending from the chamber through and below the floor, the vertical conduit including (i) a well located above the floor and within the chamber for engaging a valve stem of the inverted CoMDC and (ii) a discharge port disposed below the floor and located in a breathing tube connector;
   reciprocally engaging the valve stem with the conduit well; and
   dispensing aerosolized medicament from the inverted CoMDC through the conduit into the breathing tube connector.

17. The method of claim 16 comprising:
   guiding, with the opposing exposed edges, the counter window along the channel wherein the counter window extends outside of the sidewall.

18. The method of claim 16 wherein the vertical conduit is coaxial with the discharge port and dispenses medicament along a longitudinal axis to the breathing tube connector.

19. The method of claim 16 comprising extending at least a portion of the counter window radially outwardly through the channel and beyond the body; and
   longitudinally moving the CoMDC into the chamber.

* * * * *